United States Patent
Renlund et al.

(10) Patent No.: US 11,160,963 B2
(45) Date of Patent: Nov. 2, 2021

(54) MICRONEEDLE AND A CHIP

(71) Applicant: Ascilion AB, Kista (SE)

(72) Inventors: Markus Renlund, Åkersberga (SE); Pelle Rangsten, Storvreta (SE)

(73) Assignee: Ascilion AB, Kista (SE)

( * ) Notice: Subject to any disclaimer, the term of this patent is extended or adjusted under 35 U.S.C. 154(b) by 122 days.

(21) Appl. No.: 15/579,135

(22) PCT Filed: Dec. 2, 2016

(86) PCT No.: PCT/SE2016/051211
§ 371 (c)(1),
(2) Date: Dec. 1, 2017

(87) PCT Pub. No.: WO2017/095321
PCT Pub. Date: Jun. 8, 2017

(65) Prior Publication Data
US 2018/0161563 A1    Jun. 14, 2018

(30) Foreign Application Priority Data

Dec. 4, 2015 (SE) .................................... 1530184-9

(51) Int. Cl.
*A61M 37/00* (2006.01)
*A61B 5/145* (2006.01)
(Continued)

(52) U.S. Cl.
CPC ..... *A61M 37/0015* (2013.01); *A61B 5/14514* (2013.01); *A61B 5/14532* (2013.01);
(Continued)

(58) Field of Classification Search
CPC ...... A61M 37/0015; A61M 2037/0053; A61M 2037/003; A61B 5/150068;
(Continued)

(56) References Cited

U.S. PATENT DOCUMENTS

| | | | |
|---|---|---|---|
| 3,964,482 A | 6/1976 | Gerstel et al. | |
| 2002/0006355 A1* | 1/2002 | Whitson | A61B 5/14514 422/550 |

(Continued)

FOREIGN PATENT DOCUMENTS

| | | |
|---|---|---|
| EP | 2 283 809 A1 | 2/2011 |
| JP | 2007-504438 A | 3/2007 |

(Continued)

OTHER PUBLICATIONS

Merriam Webster Dictionary definition of "integral", available online at https://www.merriam-webster.com/dictionary/integral, accessed Sep. 25, 2019. (Year: 2019).*

(Continued)

*Primary Examiner* — Amber R Stiles
(74) *Attorney, Agent, or Firm* — Blank Rome LLP

(57) ABSTRACT

A microneedle and a chip are disclosed for extraction of fluids. The microneedle (101) provided on a substrate (102), comprises an elongated body (503) extending from a distal end (504) with a bevel (505) to a proximal end (506) on the substrate along a longitudinal axis; the elongated body comprises a capillary bore (507) extending in a longitudinal direction thereof and defines a fluid path (508); the proximal end is integrally connected with the substrate and the capillary bore is in fluid communication with a fluid channel (309) of the substrate. The cross-sectional area of the capillary bore in the distal end is larger than the cross-sectional area of the capillary bore in the proximal end.

13 Claims, 3 Drawing Sheets

(51) Int. Cl.
*A61B 5/15* (2006.01)
*A61B 10/00* (2006.01)

(52) U.S. Cl.
CPC .. *A61B 5/150022* (2013.01); *A61B 5/150282* (2013.01); *A61B 5/150396* (2013.01); *A61B 5/150969* (2013.01); *A61B 5/150984* (2013.01); *A61B 10/0045* (2013.01); *A61B 5/14546* (2013.01); *A61B 5/150068* (2013.01); *A61B 2010/008* (2013.01); *A61B 2560/0412* (2013.01); *A61M 2037/003* (2013.01); *A61M 2037/0053* (2013.01)

(58) Field of Classification Search
CPC ...... A61B 2560/0412; A61B 2010/008; A61B 5/14546; A61B 5/150969; A61B 5/150396; A61B 10/0045; A61B 5/150984; A61B 5/150282; A61B 5/150022; A61B 5/14532; A61B 5/14514
See application file for complete search history.

(56) References Cited

U.S. PATENT DOCUMENTS

| | | | | |
|---|---|---|---|---|
| 2003/0069548 | A1* | 4/2003 | Connelly | A61M 37/0015 604/264 |
| 2003/0135161 | A1 | 7/2003 | Fleming et al. | |
| 2003/0220610 | A1* | 11/2003 | Lastovich | A61M 37/0015 604/47 |
| 2004/0019331 | A1* | 1/2004 | Yeshurun | A61B 5/150282 604/173 |
| 2007/0078376 | A1* | 4/2007 | Smith | A61M 37/0015 604/21 |
| 2007/0275521 | A1* | 11/2007 | Fu | B81C 1/00111 438/197 |
| 2008/0091226 | A1* | 4/2008 | Yeshurun | A61B 10/0045 606/186 |
| 2011/0137254 | A1* | 6/2011 | Scholten | B81C 1/00111 604/173 |
| 2013/0296824 | A1* | 11/2013 | Mo | A61M 5/1454 604/506 |

FOREIGN PATENT DOCUMENTS

| | | |
|---|---|---|
| JP | 2013-169404 A | 9/2013 |
| KR | 10-2009-0059971 A | 6/2009 |
| WO | WO 02/17985 A2 | 3/2002 |
| WO | WO 03/020359 A2 | 3/2003 |
| WO | WO 2004/000389 A2 | 12/2003 |
| WO | WO 2005/060621 A2 | 7/2005 |
| WO | WO 2009/072830 A2 | 6/2009 |
| WO | WO 2014/016579 A1 | 1/2014 |
| WO | WO 2014/088492 A1 | 6/2014 |
| WO | WO 2015/009524 A1 | 1/2015 |

OTHER PUBLICATIONS

Merriam-Webster Dictionary definition 1c for "integral" available online as of Mar. 11, 2021 at merriam-webster.com/dictionary/integrally (Year: 2021).*

* cited by examiner

MICRONEEDLE AND A CHIP

TECHNICAL FIELD

The present invention relates in general to a microneedle and a chip for sampling of bodily fluids. The present invention relates in particular to microneedles provided on a substrate. The microneedle comprises an elongated body extending from a distal end with a bevel to a proximal end on the substrate along a longitudinal axis, and the elongated body comprises a capillary bore extending in a longitudinal direction thereof and defines a fluid path, and the proximal end is connected to the substrate, and the capillary bore is in fluid communication with a fluid channel of the substrate.

BACKGROUND

Although many application fields exist for microneedles, the vast majority of published microneedles concern drug delivery in various forms. The concept of an array of miniaturized needles for drug delivery purposes dates back to the 70's U.S. Pat. No. 3,964,482. One of the earliest reported microneedles in the scientific literature was an out-of-plane silicon needle array featuring 100, 1.5 mm long, needles on an area of 4.2 mm×4.2 mm in "A silicon-based, three-dimensional neural interface: manufacturing processes for an intercortical electrode array.", IEEE Trans Biomed Eng. 1991 August; 38(8):758-68, Campbell et al. Eventually bio sensing technology will be to the 21st century what microelectronics was to the second half of the 20th century. Integrated circuits (IC) have had an enormous impact on our daily life today and making use of the same miniaturization and cost benefits of volume manufacturing bio sensing might move clinical diagnosis and health monitoring from expensive laboratories to small hand-held consumer devices. Sampling of an analyte to be measured is a prerequisite for bio sensing. Many of the designs described in scientific papers have the purpose of extracting bodily fluids i.e. blood or interstitial fluid, ISF. Successful extraction of blood has been demonstrated with use of the natural "overpressure" in the vascular system. However, successful extraction of ISF without under-pressure, through diffusion or other mechanisms are rare or even non-existing.

SUMMARY OF THE INVENTION

The aim of the present invention is to set aside the abovementioned drawbacks and shortcomings of the previously known microneedles and to provide an improved solution.

An object of the invention is to provide an improved microneedle of the initially defined type which allows easy sampling of interstitial fluid, ISF.

The object of the invention is met in a microneedle and a chip respectively as defined in the appending claims.

In a first aspect, the present invention relates to a microneedle provided on a substrate, comprising: an elongated body extending from a distal end with a bevel to a proximal end on the substrate along a longitudinal axis; the elongated body comprises a capillary bore extending in a longitudinal direction thereof and defines a fluid path, the proximal end is integrally connected with the substrate and the capillary bore is in fluid communication with a fluid channel of the substrate; characterized in, that: the cross-sectional area of the capillary bore in the distal end is larger than the cross-sectional area of the capillary bore in the proximal end. A bevel is referred to as a bevelled surface relative the longitudinal axis of the capillary bore.

In a second aspect, the present invention relates to a chip, comprising: a plurality of microneedles integrally formed on a substrate, each microneedle comprising: an elongated body extending from a distal end with a bevel to a proximal end on the substrate along a longitudinal axis; the elongated body comprises a capillary bore extending in a longitudinal direction thereof and defines a fluid path, wherein a cross-sectional area of the capillary bore in the distal end is larger than the cross-sectional area of the capillary bore in the proximal end; the proximal end is integrally formed with the substrate and the first fluid path is in fluid communication with a fluid channel of the substrate; and the substrate having a fluid channel which forms a fluid path, wherein the fluid channel has a width larger than the depth of the fluid channel.

Additional or alternative features of the first aspect are described below.

The cross sectional area of the capillary bore of the microneedle may gradually decrease from the distal end towards the proximal end along the longitudinal direction. This contributes to an enhanced fluid flow through the capillary bore, by means of capillary force acting on the fluid in the capillary bore.

The cross-section (crosswise to the longitudinal direction) of the capillary bore may further comprise at least one rounded corner. This contributes to the wetting of the capillary bore, which has a positive effect on the fluid flow.

The capillary bore may have a triangular cross-section. A triangular cross-section has been demonstrated to provide a very good fluid flow in the capillary bore. A triangular cross-section within this application encompasses cross sections with substantially triangular shape, i.e. edges with convex or concave shape or straight shape, corners with sharp angles and corners with blunt angles as well as rounded corners.

The walls of the capillary bore may comprise hydrophilic surfaces, which enhances the fluid flow in the capillary bore.

The fluid channel may be configured to provide an under-pressure, relative the atmospheric pressure, to the capillary bore, whereby fluid flow through the capillary bore is enhanced. An under-pressure may for example be created with a syringe connected to the fluid channel.

The elongated body of the microneedle may further comprise a lateral hole extending in a radial direction relative the longitudinal direction, wherein the lateral hole is in fluid communication with the capillary bore. This has the effect that the risk for clogging in the capillary bore is reduced.

Below, alternative or additional features of the second aspect are presented.

In a chip, wherein at least a part of a wall of the capillary bore may form a part of a wall of the fluid channel, fluid flow is enhanced.

The fluid channel of a chip may comprise directional changes with an angle θ smaller than 90 degrees. By avoiding sharp bends of the fluid channel, fluid flow is enhanced.

The chip may further comprise a base substrate, which comprises a fluid port in fluid communication with the fluid channel, and which opens in the backside of the base substrate. This provides an access point to the sampled fluid which can be connected to a sensor element or further fluid channels.

The fluid port may comprise an increasing area in the longitudinal direction of the port towards the back of the base substrate. This allows a fluid tight connection to other fluid channels such as tubes or syringes.

The base substrate may be operatively connected to the substrate by means of anodic/direct bonding, which provides a strong and fluid tight seal without the risk of clogging the fluid channels with adhesive.

The plurality of microneedles on the chip may be surrounded by an edge, which is in level with the distal end of the microneedles. This has the effect that a membrane of a test subject is tensioned during engagement with the distal end of the microneedles.

BRIEF DESCRIPTION OF THE DRAWINGS

A more thorough understanding of the abovementioned and other features and advantages of the present invention will be evident from the following detailed description of embodiments with reference to the enclosed drawings, on which.

DETAILED DESCRIPTION OF EMBODIMENT

Figure 1:
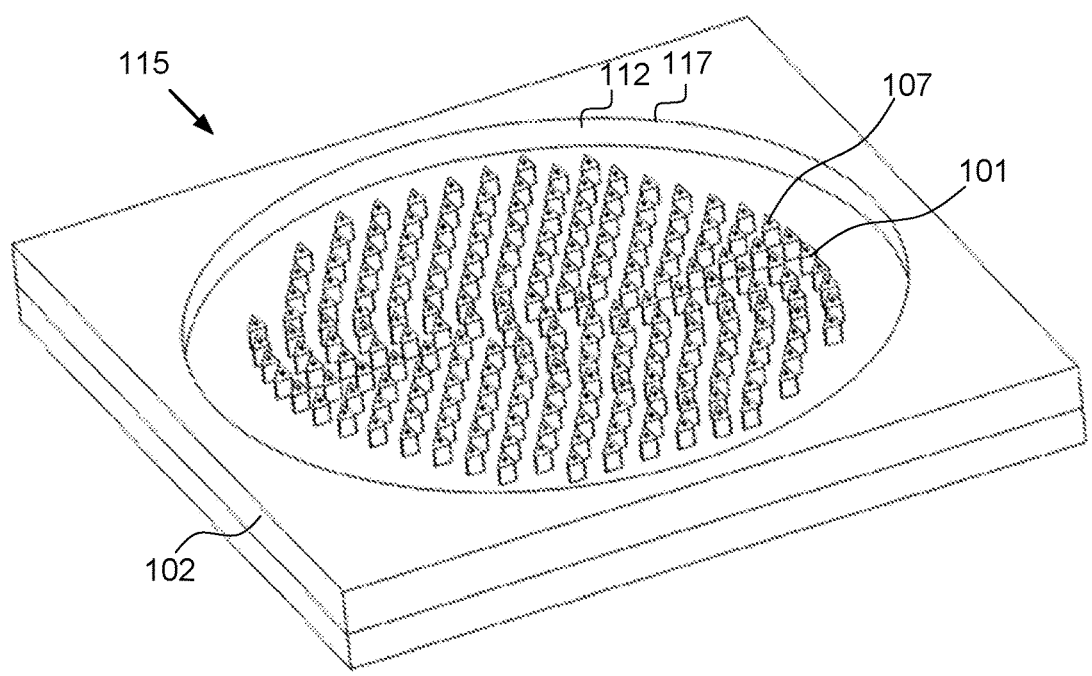
FIG. 1 is a schematic perspective view of a chip with a plurality of microneedles.

The present invention is based on the insights below. When examined carefully it's clear that the microneedles in the prior art either can't be manufactured with good yield, they are not robust enough to allow for safe use in mammals or the actual extraction is performed with several caveats described in the smallest possible font. Examples of caveats and disclaimers described in prior art are for instance that extraction only has been demonstrated on pig skin, on mammals with blisters in controlled studies or with the outmost skin layer, stratum corneum, removed prior to extraction. It's therefore safe to say that it was utterly surprising that a robust, volume manufacturable design of microneedles could be invented, designed and realized allowing for safe extraction where the extraction is performed using only capillary forces and no sub pressure or suction.

According to certain embodiments of the invention, the invention regards a design of a Microneedle chipset comprising a plurality of needles organized in an array or matrix at a minimum distance from each other of 100 micrometres but not greater than 1 mm apart, has a sharp tip in the same plane or slightly below a surrounding structure and where the tip has a 54.7 degree bevel and the needle a hollow bore with a capillary dimension that allows extraction without clogging and a shaft, longer than 200 micrometres as well as interior dimensions and geometry that allow capillary forces to act on liquid all the way to the collecting channels/voids/cavities where misaligned holes in backside channels connect.

According to some embodiments of the invention, the invention is characterized by a chipset with the above described plurality of microneedles where:

The needles have a sharp tip defined by crystallographic planes

The bevel slope of each needle is defined by the 111 planes

Each microneedle may comprise a capillary bore, e.g. a single capillary bore. Thereby bodily fluid may be extracted by means of capillary suction through the microneedle, fluid cavity and fluid exit port.

Each microneedle may be provided with a cap at a distal end for shielding the capillary bore from clogging, whereby at least one opening to the capillary bore is provided in a lateral direction of the microneedle, perpendicular to the axial or longitudinal extension of the microneedle.

The capillary bore of each microneedle may be provided with a hydrophilic surface. Thereby capillary flow of bodily fluid may be assisted.

Each microneedle may comprise a plurality of cutting elements extending along a longitudinal direction of the microneedle. Thereby the skin may be cut and opened to facilitate extraction of bodily fluid.

The perimeter of the bore hole in each microneedle as projected on the bevel of the needle is located at a distance from the tip in a way where the tip is outside the perimeter.

Each microneedle may have a length of 200-1000 μm, preferably 400-900 μm, more preferably 300-600 μm, and an outer circumference of 400-800 μm Thereby the microneedle has dimensions suitable for penetration of the skin and extraction of bodily fluid.

A portion of the bore hole as projected on the side that contains the capillary system is outside the connecting capillary generating a maximized wall surface that minimizes surface tension Each connection between the bore hole and the capillary should be designed with a minimized contact angle in order to enable tension driven flow Surfaces in contact with the fluid should be hydrophilic The shaft of each needle is without a hilt The vertical bore holes may be filled with material that is selective and specific to certain molecules and thereby creating an integrated extraction and sensing chipset. The filler material could for instance be glucose oxidase and carbon powder and thereby creating a glucose specific extraction and sensing chipset.

A plurality of openings may be provided in a lateral direction, around a circumference of the microneedle. The at least one opening may be provided about midways along a longitudinal extension of the microneedle. Thereby the extraction of bodily fluid is facilitated and the risk for clogging is further reduced.

According to some embodiments of the invention, the invention is further characterized by the above described chipset where the plurality of needles Have a frame structure dimensioned to support the tip of a finger constructed as structure protruding along the longitudinal direction of the microneedles, and preferably having a diameter of less than 15 mm.

May be at least partly surrounded by a frame structure dimensioned to support the tip of a finger. Thereby the skin of the tip of the finger may be supported and tensioned to facilitate penetration of the at least one microneedle into the skin.

Are protected by a surrounding structure protruding to at least the same plane as the tip of the needles enabling for instance handling of wafers in the case of MEMS manufacturing of the herein described chipset.

Have a surrounding structure that stretches the skin prior to penetration by the above mentioned plurality of needles.

With their hollow structure constitute inlets for sampling of bodily fluid. Thereby bodily fluid, such as interstitial fluid (ISF) may be extracted and introduced into a sensor with minimal discomfort for the patient.

Have the collecting network of capillaries in different patterns and as an advantage is collection of liquid and storage made without evaporation problems. Hence, the chip can sample and the analysis can be made ex situ.

Have the interface between the vertical bore holes and the collecting capillary laterally misaligned to allow liquid to wet the walls and hence by capillary action fill the collecting channels on the backside.

Are located at minimum distance from each other of 200 microns in order to avoid the effect of bed of nails.

Have the bevel oriented in the crystallographic directions or preferred in the same direction.

Are oriented in a way that enables connection between at least a subset of needles using integrated, for instance etched, capillaries.

Could all be combined with a capillary system enabling a capillary flow to a fluid exit port.

Configurations

In another configuration may the above described sampling chipset be used in conjunction with a sensing unit. The sensing unit may be wafer bonded or attached to the extraction chipset by other means but may also be connected through capillary tubing or an equivalent flow system.

The sensing unit may be configured for detecting a level of glucose in bodily fluid, i.e. a glucose sensor. Thereby a sensor for rapid and accurate detection of the level of glucose in bodily fluid may be provided.

The sensor may be configured for detecting a concentration or presence of lactate, carbon dioxide, or other molecules in bodily fluid. Thereby a sensor for rapid and accurate detection of the level of above mentioned molecule or other molecules, ions or biomarkers in bodily fluid may be provided.

In a first embodiment of the present invention, a chip, generally designated 115, is shown in a perspective view in FIG. 1. The chip 115 comprises a substrate 102 with a plurality of microneedles 101 arranged thereon. Each of the microneedles comprises a capillary bore 107, which extends through the microneedle and the substrate 102. In the above paragraphs the capillary bore 107 is denoted vertical hole. The substrate 102 further comprises a surrounding wall 112 with an upper edge 117. The upper edge 117 may have the same height as the microneedles. This proves to be very useful if a finger of a test subject is supposed to interact with the microneedles, since a tensioning effect of the skin is achieved.

Figure 2:
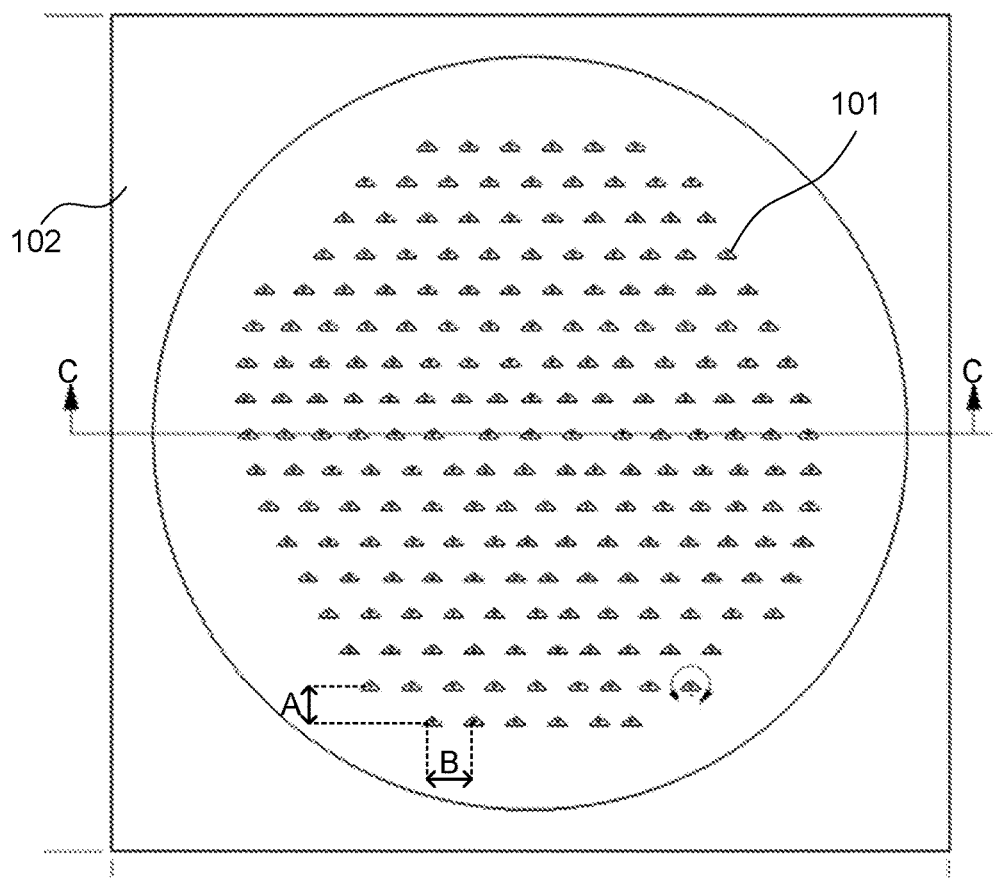
FIG. 2 is a schematic top view of a chip with a plurality of microneedles.

In FIG. 2 the chip of FIG. 1 is shown from above. This view shows the arrangement of the microneedles 101 on the substrate 102. The microneedles 101 are preferably arranged with a minimum distance, A and B, of 200 um between neighbouring microneedles in order to avoid the bed of nails effect. However, the distance between neighbouring microneedles may be in the interval from 100 um to 1 mm. In this view a line C-C is also illustrated and this imaginary line will be used later to define a cross section through the substrate and the microneedles.

Figure 3:
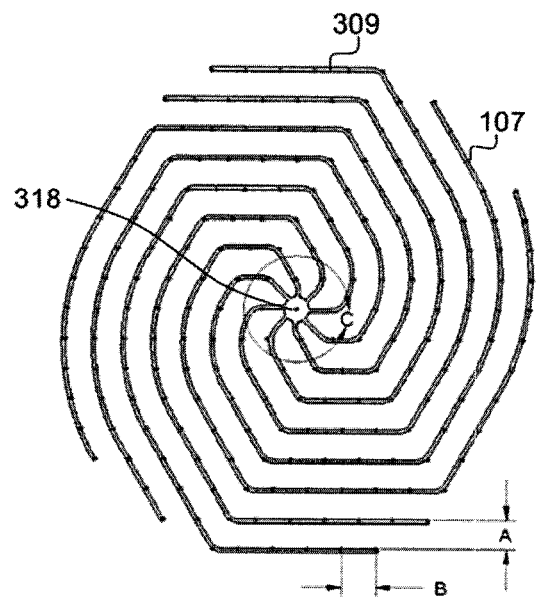
FIG. 3 is a bottom view of a substrate with fluid channels.

In FIG. 3 a pattern of fluid channels 309 which provides fluid communication between the microneedles is illustrated. This figure is a view from the backside of the substrate 102. In this view the capillary bores 107 of the microneedles are shown and opens into the fluid channels 309 of the substrate 102. The fluid channels 309 are shallow with a width that preferably is larger than a corresponding depth. The fluid channels may comprise a decreasing cross-sectional area in order to further enhance the fluid flow in the fluid channel (not illustrated). The fluid channels are arranged in spiral pattern around a fluid channel port 318. In one embodiment the pattern of fluid channels may comprise a peripheral flow path which connects capillary bores of the peripheral microneedles (not illustrated). This has the effect that even if a fluid channel 309 is clogged, fluid flow is allowed to the fluid channel port 318.

Figure 4:
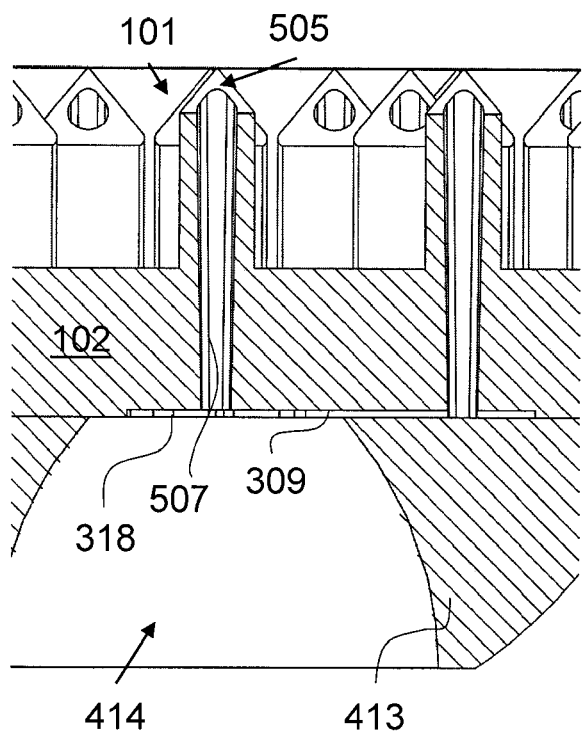
FIG. 4 is cross-sectional view along the line C-C in FIG. 2.

FIG. 4 is a cross sectional view along the imaginary line C-C through a row of microneedles and the substrate 102. Thus, the substrate is cut open and viewed from a side view. In this figure a microneedle 101 is shown cut-open. The microneedle comprises a bevel 505 defined by crystallographic planes of the material of the microneedle. The capillary bore 507 is in fluid communication with the fluid channel port 318 and the fluid channel 309. The substrate 102 is operatively connected to a base substrate 413, which comprises a fluid port 414. The fluid port 414 may comprise sloped sidewalls, which provides an easy and fluid tight connection to other devices. The base substrate 413 may be operatively connected to the substrate 102 by means of bonding, for example anodic or direct bonding, which are well known in the art.

Figure 5:
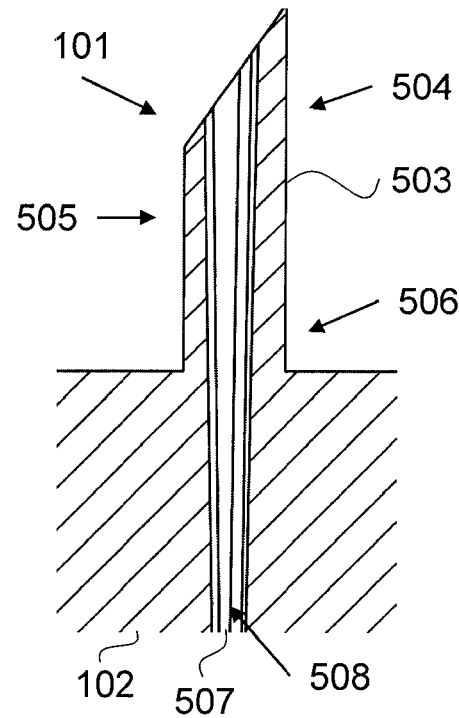
FIG. 5 is a cross-sectional view of a microneedle.

The microneedle 101 is further illustrated in FIG. 5 in which a microneedle is cut open. The microneedle 101 comprises an elongated body 503 with a distal end 504 and a proximal end 506 on the substrate 102. In this embodiment the microneedle is integrally formed from the substrate. Such a manufacturing process may involve the following process steps:

Define the elongated body 503 by means of photolithography, PL, and dry etching of the substrate 102, using for example Deep Reactive-Ion Etching, DRIE.

Define the bevel 505 of the distal end 504 using anisotropic wet-etching.

Define the mask for the capillary bore 507, by means of applying photo-resist on the substrate 102, followed by PL which defines a mask with an opening on the bevel 505.

Etching of the capillary bore 507 from the front side of the substrate 102 through the mask opening on the bevel 505.

In the exemplary process outlined above, the photo resist applied to the substrate 102 may be spray coating resist or dry film resist. The bevel 505 of the distal end 504 provides a sharp edge particularly suitable for bio sensing applications. The capillary bore 507 opens in the bevel 505 such that a distance between the periphery of the capillary bore 507 and the tip of the sharp edge of the bevel is obtained. The capillary bore 507 extends from the bevel 505 of the distal end 504 of the elongated body 503 towards the proximal end 506 on the substrate 102. The cross sectional area of the capillary bore in the distal end 504 is larger than the cross-sectional area of the capillary bore 507 in the proximal end 506. This way capillary action is enhanced and the fluid flow through the capillary bore 507 increases.

Figure 6:
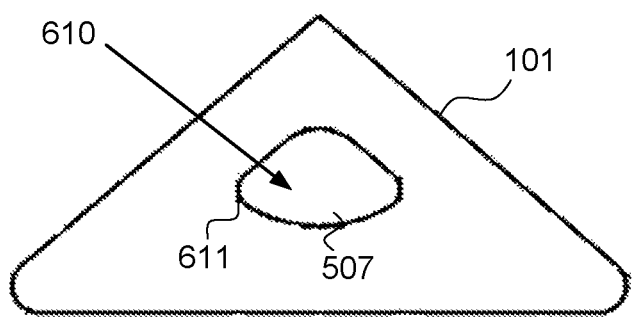
FIG. 6 is a cross-sectional view along the longitudinal axis of a microneedle.

An embodiment of the microneedle 101 is shown from above in FIG. 6. In this figure the triangular cross-section 610 of the capillary bore 507 is shown. In this application a triangular cross-section should encompass a shape with three edges connected with corresponding corners. The edges may be straight, curved, convex or concave. The corners may be sharp, blunt or rounded with different or the same radius. Thus, within this application a cross-section with the shape of an egg or a heart is considered to be triangular. The triangular shape of the capillary bore 610. In FIG. 6 the shape of the capillary bore 507 is substantially triangular with a convex base connected to straight sections via a curved corner 611. This shape of the capillary bore 507 has been demonstrated to be very efficient for extracting interstitial fluid from a finger of a human test subject.

Figure 7:
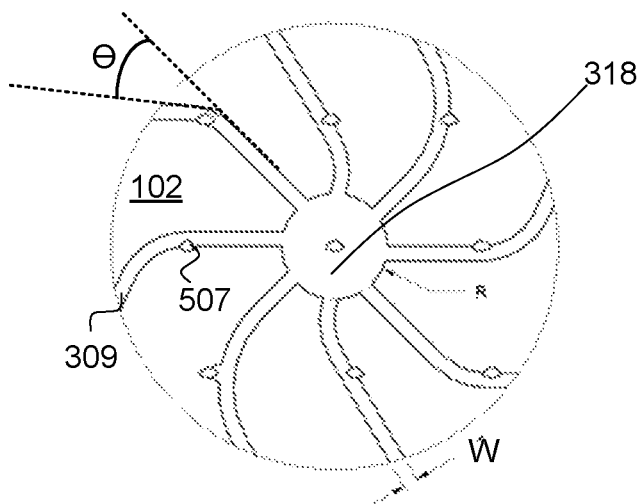
FIG. 7 is a bottom view of the substrate with fluid channels.

In FIG. 7 a magnified view of the backside of the substrate 102 is shown. The fluid channel port 318 of the backside of the substrate 102 is connected to a number of fluid channels 309. In this figure the width of the fluid channel 309 is designated W and the curved angle is designated θ. In order to provide a tension driven fluid flow, the maximum curved angle is 90 degrees. The capillary bores 507 are also connected to the fluid channels 309 such that at least a part of a wall 916 of the capillary bore forms a part of a wall of the fluid channel 309. This is further illustrated in FIG. 9.

Figures 8, 9:
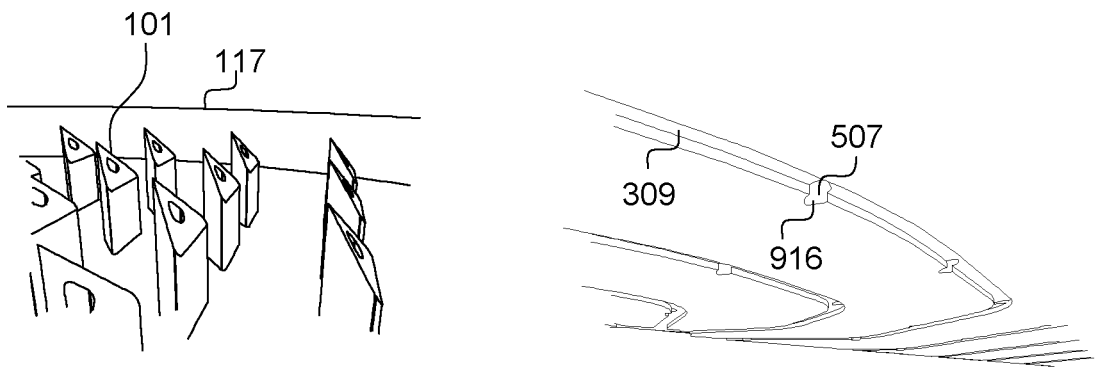
FIG. 8 is a schematic perspective view of the microneedles on the substrate.
FIG. 9 is a schematic perspective view of the backside of the substrate with fluid channels and capillary bores.

Finally, in FIG. 8 it is illustrated that the distal end of the microneedles 101 are in level with the upper edge 117. This edge provides a tensioning effect of the skin upon contact between the skin and the chip.

Additional features that are disclosed in relation to the first embodiment can also be applied to the second embodiment.

In one embodiment is the substrate 102 made of silicon, and the base substrate 413 is made of glass.

The claims attached are drafted to define the scope of invention including the embodiments disclosed and modifications and implementations thereof which can be derived from the disclosure.

The invention claimed is:

1. A microneedle provided on a substrate, comprising:
   an elongated body extending from a distal end thereof with a bevel to a proximal end on the substrate along a longitudinal axis, wherein:
      the elongated body comprises a capillary bore having a hydrophilic surface and extending in a longitudinal direction thereof and defining a fluid path for sampling of bodily fluids;
      the proximal end is connected to the substrate and the capillary bore is in fluid communication with a fluid channel of the substrate; and
      the capillary bore has a cross-sectional area in the distal end which is larger than the cross- sectional area of the capillary bore in the proximal end, and wherein the cross-sectional area of the capillary bore gradually decreases from the distal end to the proximal end of the elongated body along the longitudinal direction, thereby enhancing capillary action and increasing fluid flow through the capillary bore.

2. A microneedle according to claim 1, wherein the cross-section of the capillary bore comprises a triangular cross-section in a perpendicular direction relative the longitudinal direction of the microneedle.

3. A microneedle according to claim according to claim 1, wherein the cross-section of the capillary bore further comprises at least one rounded corner.

4. A microneedle according to claim 1, wherein the fluid channel is configured to provide an under-pressure, relative the atmospheric pressure, to the capillary bore, whereby fluid flow through the capillary bore is promoted.

5. A microneedle according to claim 1, wherein the elongated body further comprises a lateral hole from a side of the microneedle and extends in a radial direction relative the longitudinal direction, wherein the lateral hole is in fluid communication with the capillary hole.

6. A chip, comprising:
   a plurality of microneedles integrally formed on a substrate, each microneedle comprising:
      an elongated body extending from a distal end thereof with a bevel to a proximal end thereof on the substrate along a longitudinal axis;
      wherein the elongated body comprises a capillary bore having a hydrophilic surface and extending in a longitudinal direction thereof and defining a fluid path for sampling of bodily fluids, wherein a cross-sectional area of the capillary bore in the distal end is larger than the cross-sectional area of the capillary bore in the proximal end, and wherein the cross-sectional area of the capillary bore gradually decreases from the distal end to the proximal end of the elongated body along the longitudinal direction, thereby enhancing capillary action and increasing fluid flow through the capillary bore; and
      wherein the proximal end is integrally formed with the substrate and the fluid path is in fluid communication with a fluid channel of the substrate.

7. A chip according to claim 6, wherein the fluid channel of the substrate has a width larger than a depth of the fluid channel.

8. A chip according to claim 6, wherein at least a part of a wall of the capillary bore forms a part of a wall of the fluid channel.

9. A chip according to claim 6, wherein the fluid channel comprises directional changes with an angle (θ) smaller than 90 degrees.

10. A chip according to claim 6, further comprising a base substrate, which comprises a fluid port in fluid communication with the fluid channel, and which opens in a backside of the base substrate.

11. A chip according to claim 10, wherein the fluid port comprises an increasing area in a longitudinal direction of the fluid port towards the backside of the base substrate.

12. A chip according to claim 10, wherein the base substrate is operatively connected to the substrate by means of bonding.

13. A chip according to claim 6, wherein the plurality of microneedles are surrounded by an edge which has a height equal to a height of the microneedles, such that the edge is aligned with the distal end of the microneedles.

* * * * *